US009956307B2

(12) United States Patent
Burapachaisri et al.

(10) Patent No.: US 9,956,307 B2
(45) Date of Patent: May 1, 2018

(54) METHODS AND APPARATUS FOR TREATMENT OF LUER CONNECTORS

(71) Applicant: CatheCare LLC, New York, NY (US)

(72) Inventors: Aonnicha Burapachaisri, Bangkok (TH); Chanond Sophonpanich, Bangkok (TH); Charles Pan, Forest Hills, NY (US); Aishwarya Raja, Woodbridge, VA (US)

(73) Assignee: CatheCare LLC, New York, NY (US)

( * ) Notice: Subject to any disclaimer, the term of this patent is extended or adjusted under 35 U.S.C. 154(b) by 0 days. days.

(21) Appl. No.: 15/484,477

(22) Filed: Apr. 11, 2017

(65) Prior Publication Data

US 2017/0232123 A1 Aug. 17, 2017

Related U.S. Application Data

(60) Provisional application No. 62/331,469, filed on May 4, 2016.

(51) Int. Cl.
*A61L 2/10* (2006.01)
*A61M 39/10* (2006.01)

(52) U.S. Cl.
CPC ............... *A61L 2/10* (2013.01); *A61M 39/10* (2013.01); *A61L 2202/14* (2013.01); *A61L 2202/24* (2013.01); *A61M 2209/10* (2013.01)

(58) Field of Classification Search
CPC ........................................................ A61L 2/10
See application file for complete search history.

(56) References Cited

U.S. PATENT DOCUMENTS

| 4,620,845 A * | 11/1986 | Popovich ................. A61L 2/10 604/28 |
| 4,876,632 A * | 10/1989 | Osterhout .............. G01R 15/04 320/DIG. 21 |
| 5,199,948 A | 4/1993 | McPhee |
| 7,834,328 B2 | 11/2010 | Redmond et al. |
| RE43,142 E | 1/2012 | Jepson et al. |
| 8,197,087 B2 | 6/2012 | Sobue et al. |
| 8,403,894 B2 | 3/2013 | Lynn et al. |
| 8,460,220 B2 | 6/2013 | Dacey, Jr. et al. |

(Continued)

FOREIGN PATENT DOCUMENTS

| CA | 2447881 | 12/2002 |
| WO | 02/102419 A3 | 12/2002 |

(Continued)

OTHER PUBLICATIONS

"Integrated Circuit". Wikipedia. Version from Apr. 21, 2015.*

(Continued)

*Primary Examiner* — Donald R Spamer
(74) *Attorney, Agent, or Firm* — DLA Piper LLP (US)

(57) ABSTRACT

Devices, methods, and systems for a luer connector treatment device are described herein. The luer connector treatment device may include one or multiple sources of UV radiation configured to emit UV radiation capable of sterilizing the contents of a treatment chamber while a first medical device (e.g., catheter) is connected to a secondary medical device, and while the first medical device is separate from a secondary medical device. Sources of UV radiation may be located along both a cap and body of the luer connector treatment device.

24 Claims, 9 Drawing Sheets

(56) References Cited

U.S. PATENT DOCUMENTS

| | | |
|---|---|---|
| 8,469,545 B2 | 6/2013 | Sobue et al. |
| 8,556,950 B2 | 10/2013 | Rioux et al. |
| 8,585,627 B2 | 11/2013 | Dacey, Jr. et al. |
| 8,779,386 B2 | 7/2014 | Bak |
| 8,911,109 B2 | 12/2014 | Sobue et al. |
| 8,933,416 B2 | 1/2015 | Arcand et al. |
| 8,946,653 B2 | 2/2015 | Victor et al. |
| 9,295,742 B2 | 3/2016 | Rasooly et al. |
| 9,408,929 B2 | 8/2016 | Ma |
| 9,421,290 B2 | 8/2016 | Victor et al. |
| 2003/0017073 A1* | 1/2003 | Eckhardt .................. A61L 2/10 422/24 |
| 2006/0009821 A1 | 1/2006 | Perez |
| 2006/0216193 A1 | 9/2006 | Johnson et al. |
| 2007/0176117 A1 | 8/2007 | Redmond et al. |
| 2008/0027399 A1 | 1/2008 | Harding et al. |
| 2009/0048648 A1 | 2/2009 | Dacey, Jr. et al. |
| 2010/0072399 A1* | 3/2010 | Street .................. A61L 2/10 250/492.1 |
| 2011/0213339 A1 | 9/2011 | Bak |
| 2013/0303996 A1 | 11/2013 | Rasooly et al. |
| 2013/0323119 A1* | 12/2013 | Alwan .................. A61L 2/10 422/24 |
| 2014/0249487 A1 | 9/2014 | Lynn et al. |
| 2014/0334974 A1 | 11/2014 | Rasooly et al. |
| 2015/0148776 A1 | 5/2015 | Sobue et al. |
| 2015/0165185 A1 | 6/2015 | Cohen et al. |
| 2015/0209457 A1 | 7/2015 | Bonutti et al. |
| 2015/0284520 A1* | 10/2015 | Ozawa .................. C08L 33/10 526/282 |
| 2015/0290347 A1 | 10/2015 | Braden et al. |

FOREIGN PATENT DOCUMENTS

| | | |
|---|---|---|
| WO | 2009/006506 A1 | 1/2009 |
| WO | 2015/157662 A1 | 10/2015 |

OTHER PUBLICATIONS

"Chamber". Collins English Dictionary. 2014. Retrieved from thefreedictionary.com. (Year: 2014).*

The International Search Report and Written Opinion dated Aug. 24, 2017 of corresponding International Application No. PCT/US17/28269.

* cited by examiner

METHODS AND APPARATUS FOR TREATMENT OF LUER CONNECTORS

TECHNICAL FIELD

The present disclosure relates to the technical field of ultraviolet irradiation systems as used in treatment devices. An exemplary embodiment add-on or integrated treatment devices.

BACKGROUND

Globally, hospital acquired infections pose a major burden to patients. According to the Centers for Disease Control and Prevention (CDC), hospital acquired infections affect about one in twenty-one patients. Accounting for over 250,000 cases annually, catheter-related bloodstream infections (CRBSIs) are one of the most common hospital acquired infections. CRBSIs can lead to bacteremia and septicemia in hospitalized patients. Notably, septicemia, which is a systemic response to the presence of bacteria in the bloodstream, poses a serious health hazard to patients and is associated with a mortality rate of up to 30%. Dealing with the sequelae of bloodstream infections such as septicemia is a major financial burden to the healthcare system and is believed to cost at least $7 billion every year.

The primary source of CRBSIs is thought to be microflora colonization on the catheter hub and subsequent ingress of the microflora into the catheter lumen. Indeed, microflora colonization is believed to account for 54% of all CRBSIs. The catheter hub, the site at which fluids and drugs are injected into the bloodstream, is a common source for infection because it is frequently handled and manipulated by healthcare personnel and in close proximity to a patient's skin and/or clothing as well as the exogenous hospital environment that is often ridden with microbes. Typically, the catheter hub contains a luer connection system.

In an effort to reduce the impact of CRBSIs, the CDC has issued guidelines that describe various ways to minimize bloodstream infection rates in hospital, outpatient, and home care settings. The guidelines provide protocols for hand hygiene, catheter site care, and admixture preparation, that when followed, are expected to reduce the number of CRBSIs. However, despite these CDC guidelines and attempts to educate healthcare personnel on the correct procedure to disinfect the catheter hub and luer connectors, infections continue to plague healthcare systems at relatively unchanged rates. In fact, a gap analysis study identified inadequate catheter maintenance as the main cause of CRBSIs. Specifically, health care providers were not consistently scrubbing the hub with alcohol for the required 15 seconds before accessing the line. Accordingly, there is a need for more robust systems and methods for treating luer connectors that is immune to human error and inconsistencies.

The prior art describes a variety of systems and devices to treat the luer connectors and prevent downstream CRBSIs. One method for preventing downstream CRBSIs utilizes an antibiotic. For example, once a catheter is suspected of infection due to a patient displaying symptoms like inflammation and redness at the site of insertion, first-line therapy with locally administered intraluminal antibiotics such as ethanol or antibiotic lock therapy may be used. While not routinely utilized for the prophylaxis of infections, the guidelines from the Infectious Diseases Society of America encourage the use of antibiotic lock solutions with vancomycin, gentamicin, cefazolin, or ethanol as a therapeutic option for intraluminal infections when the catheter is difficult to remove. The use of an antibiotic lock solution is appealing for localized infections because it is easy to use and associated with low costs and minimal systemic side effects if the catheter remains closed. Generally, antibiotics are recommended in a short-term regimen of 7 to 14 days. The main disadvantage with antibiotic locks is the increased risk of bacterial resistance. Specifically, biofilm-forming species like *Staphylococcus* have been shown to become resistant to methicillin and vancomycin. Accordingly, there is a need for methods and systems for treating a luer connectors that are prophylactic and do not contribute to bacterial resistance.

Another method for treating the luer connectors and preventing CRBSIs is the use of ethanol caps. For example, 3M™ Curos™ Disinfecting Port Protectors use 70% isopropyl alcohol (IPA). In particular, these port protectors contain 70% IPA that bathes the surface of the luer connector when the luer engages with the port protector. The port protectors disinfect the surface of the luer connector after 1 minute of contact. Notably, the Curos™ Disinfecting Port Protectors can only maintain sterility when the hub is not in use. When the cap is removed to inject fluids or drugs into the catheter, the sterile environment is contaminated.

Similar to the mechanism utilized by 3M™ Curos™ Disinfecting Port Protectors, ICU Medical's SwabCap® also utilizes a 70% IPA solution. In particular, the SwabCap® includes a 70% IPA Sponge that bathes the threads and top connectors of the luer for needlefree connectors on catheters. Additionally, the SwabCap® includes a thread cover design that is configured to disinfect the connector surface and threads of the catheter. Like, 3M™ Curos™ Disinfecting Port Protectors, SwabCap® also fails to disinfect the luer connector when it is in use. For example, incoming bacteria from a syringe or needleless connector cannot be eradicated by the mechanism used by SwabCap®. Moreover, as the SwabCap® only disinfects the top surface of the needle free connector's threads, other portions of the hub such as the intraluminal surfaces remain vulnerable to contamination.

Accordingly, there is a need for methods and systems for treating a luer connector that provide treatment to the luer connector, even while a cap for the catheter hub is removed and/or a syringe, needleless connector or the like is attached to the catheter hub.

SUMMARY

An exemplary embodiment of the disclosed luer connector treatment device, systems and methods provide more robust systems and methods for treating luer connectors in a manner that reduces the likelihood of human error. An exemplary embodiment of the device provides methods and systems for treating a luer connector that applies treatment to the luer connector, including when a cap for the catheter hub is removed and/or a syringe, needleless connector, or the like is attached to the catheter hub. Additionally, the device intends to minimize its contributions towards bacterial resistance and may be used prophylactically.

In one exemplary embodiment, a luer connector treatment device includes a first housing component and a second housing component. The second housing component may be reversibly coupled to the first housing component and may include a treatment chamber including at least two luer connectors. At least one of the first housing component and the second housing component has at least one source of ultraviolet (UV) radiation. The at least one source of UV radiation of the first housing component may be configured to emit UV radiation into the treatment chamber when the first housing component is engaged with the second housing component. Additionally, the at least one source of UV radiation of the second housing component may be configured to emit UV radiation into the treatment chamber when the first housing component is either engaged with or disengaged from the second housing component.

In another exemplary embodiment, a method of treating a luer connector includes providing a luer connector treatment device further comprising a first housing component and a second housing component, the first housing component having at least one source of UV radiation, and the second housing component having at least one source of UV radiation and a treatment chamber including at least two luer connectors, wherein the first housing component is reversibly coupled to the second housing component. The method also includes engaging a first medical device with one of the at least two luer connectors, disengaging the first housing component from the second housing component, engaging a second medical device with at least one remaining luer of the at least two luer connectors to form a fluidic channel between the first medical device and the second medical device, treating the treatment chamber while the first housing component is disengaged from the second housing component by applying UV radiation to the treatment chamber by way of the at least one source of UV radiation on the second housing component, disengaging the second medical device from the at least one remaining luer of the at least two luer connectors, engaging the first housing component to the second housing component and treating the treatment chamber while the first housing component is engaged with the second housing component by applying UV radiation to the treatment chamber by way of the at least one source of UV radiation on the first housing component and/or the at least one source of UV radiation on the second housing component.

BRIEF DESCRIPTION OF THE DRAWINGS

The accompanying drawings incorporated in and forming a part of this specification illustrate several aspects of the disclosure, and together with the description serve to explain the principles of the disclosure.

DETAILED DESCRIPTION OF THE DRAWINGS

Aspects of the present disclosure relate to systems, methods and devices related to a luer connector treatment device. As will be discussed in further detail below, advantageously, the disclosed device may be integrated with standardized luer connections, is compliant with current medical procedures, is easy to use, requires little to no daily maintenance by healthcare personnel, can withstand the pressures of blood infusion, drug or fluid infusion, and clot busting, may be adherent with FDA regulations surrounding catheter devices, is compatible with clinically acceptable treatment methods, is non-toxic and biocompatible, does not enhance the risk of bacterial resistance and will not interfere with existing drug delivery mechanisms.

Figure 1:
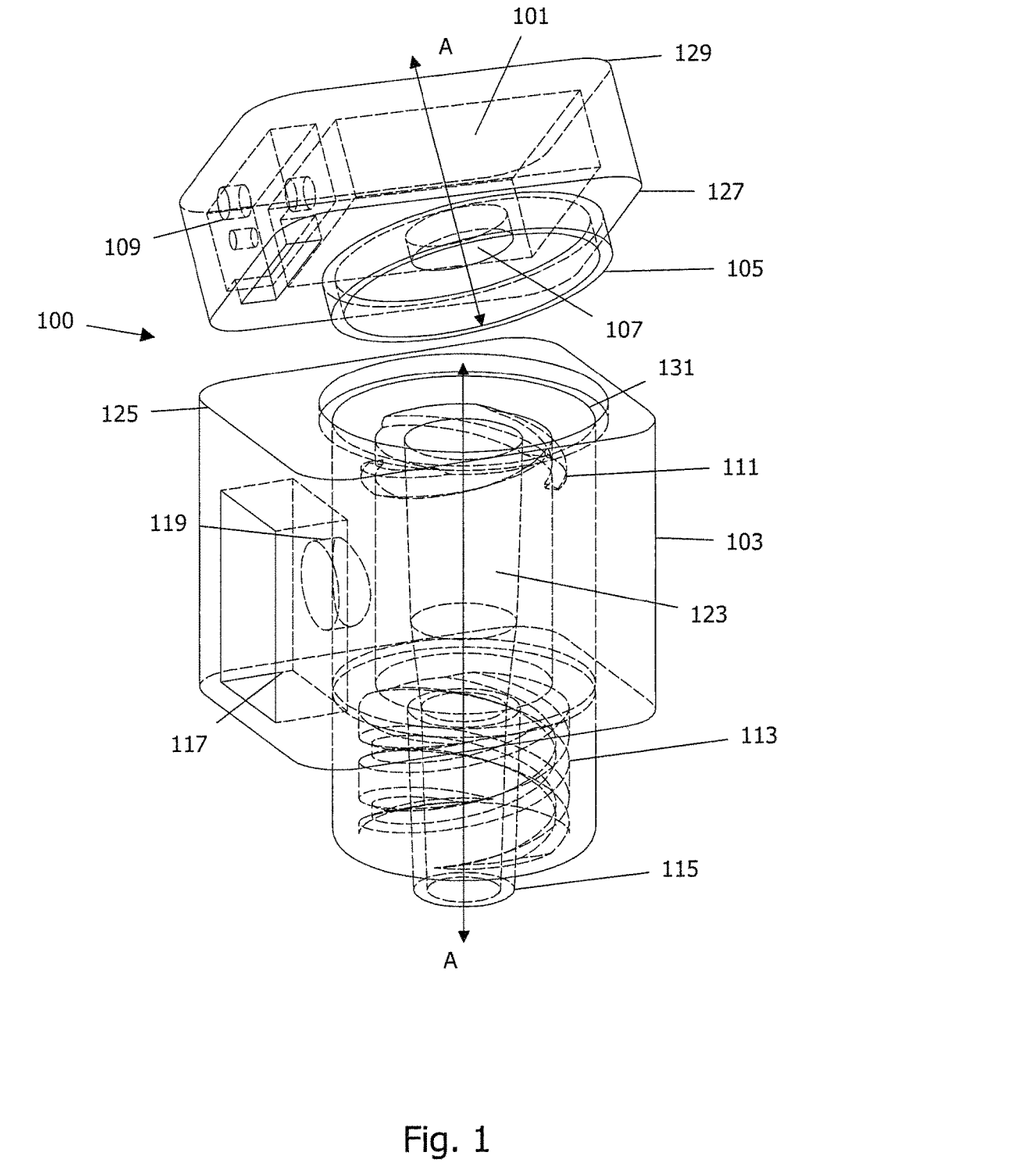
FIG. 1 illustrates a perspective view of an exemplary embodiment of the device.

FIG. 1 illustrates a luer connector treatment device 100 having a first housing component, which may be a cap 101. In one embodiment, the cap 101 may include the at least one source of UV radiation. The luer connector treatment device 100 may also have a second housing component, a body 103 that includes a treatment chamber 123 and the at least one source of UV radiation. In the embodiment of the luer connector treatment device 100 depicted in FIG. 1, the cap 101 and body 103 are configured to emit UV radiation to treat contents of the treatment chamber 123. Contents of the treatment chamber 123 may include areas surrounding the at least two luer connectors 113 and 111, in between the at least two luer connectors, and surrounding junction points where the luer connector treatment device 100 forms a connection with other medical devices such as a catheter hub. As depicted, the body 103 may have a first end 115 proximate the catheter and a second end 125 proximate the cap 101. As illustrated, in one embodiment the body 103 may have a substantially rectangular prism shape with rounded edges and surround a cylindrical treatment chamber 123 having an axis A. In the illustrated embodiment, the cap 101 also has a substantially rectangular prism shape with a cylindrical opening such that the cap 101 may be used to cover the cylindrical treatment chamber 123. Although a substantially rectangular prism shape and cylindrical shape is illustrated in FIG. 1, it is contemplated that any shapes that allow for a catheter to connect to a syringe or other medical device may be used for each of the body 103, cap 101, and treatment chamber 123. In one embodiment, the shape of the body 103 and cap 101 may be designed with smooth surfaces so as to provide additional comfort to the user and prevent the adherence of bacteria along or inside the body 103 or cap 101.

In one embodiment, the body 103 may contain one or more apertures 117 configured to hold the at least one source of UV radiation 119. The one or more apertures 117 may be positioned about or near the peripheral of the treatment chamber 123 and the at least one source of UV radiation 119 may be embedded within the aperture 117. Similarly, the cap 101 may contain one or more apertures 107 also configured to hold one or more sources of UV radiation. Additionally the cap 101 may include additional apertures 109 configured to hold electrical wires and/or cables that connect the cap 101 and the body 103. In one embodiment, the one or more apertures 107 may be positioned within the cap 101 such that the sources of UV radiation emit radiation into the treatment chamber 123 of the body 103 in a generally downwards direction along an axis A. UV radiation emitted from the at least one source of UV radiation contained within the apertures 107, 117 may be configured to cover the interior volume of the treatment chamber 123 including the contents of the treatment chamber 123. The apertures 107, 117 may be shaped so as to conform to the shape of the respective source of UV radiation held within it. In one embodiment, the sources of UV radiation 119 may be located in a substantially circular aperture, and wires, PCB boards, and/or leads associated with the source of UV radiation may extend along the body 103 or be contained within other apertures 117.

The treatment chamber may include one or more luer connectors. In one embodiment, standardized luer connectors may be used. Standardized luer connectors are commonly used for the fluid-tight connections of medical apparatus and instruments. Standardized luer connectors are typically conical in shape with a six percent (6%) gradient. The use of standardized luer connectors may be advantageous as it allows the luer connector treatment device to be compatible with existing medical devices and techniques used by healthcare personnel.

In one embodiment, the treatment chamber 123 includes a male luer connector 113 having protruding threads, and a female luer connector 111 having a surface with threads configured to engage with that on any external male luer connectors. In such an embodiment, the male luer connector 113 may be configured to engage with a catheter, and the female luer connector 111 with a secondary medical device. Catheters that may be used with the disclosed luer connector treatment device include (but are not limited to) central venous catheters, gastrostomy catheters, cardiovascular catheters, lung catheters, urinary catheters and the like. Secondary medical devices include a medical syringe, hemodialysis machine, IV drip, drug infusers, blood samplers, needle ports, Y-adapters, flow adjustment valves, drip indicators, fluid bags and the like.

Figures 6A, 6B:
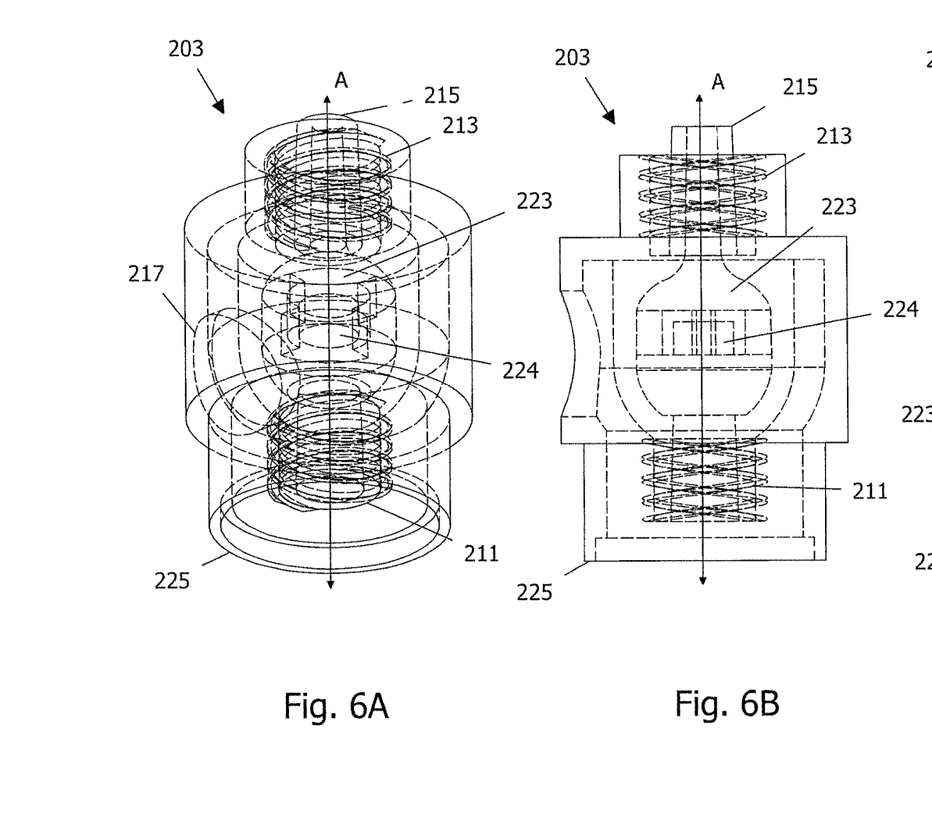
FIG. 6A illustrates a bottom perspective view of a secondary housing component of another alternative exemplary embodiment of the device.
FIG. 6B illustrates a cross-sectional view of the secondary housing component depicted in FIG. 6A.
Figure 6C:
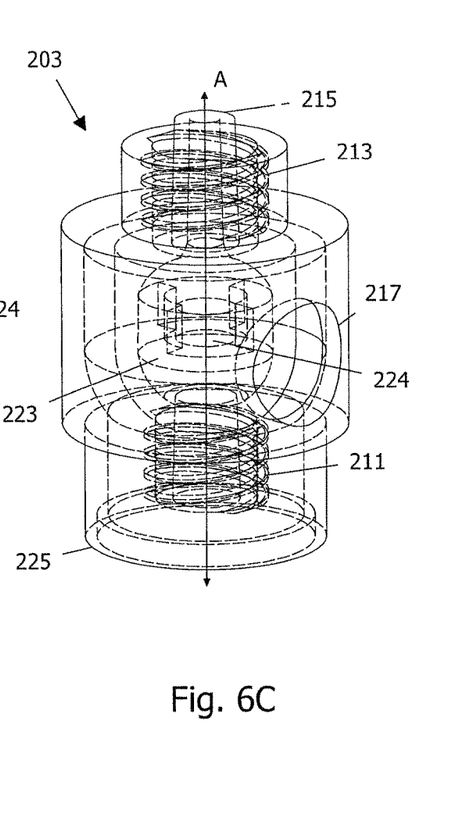
FIG. 6C illustrates a top perspective view of the secondary housing component depicted in FIGS. 6A-6B.

A fluidic channel may be formed between the male luer connector 113 and the female luer connector 111 within the treatment chamber 123 such that fluid may flow between the catheter and the secondary medical device attached to each of the respective luer connectors. The fluidic channel may provide a low-resistance, bi-directional fluid path into and out of the patient's body. The fluidic channel may be configured such that removal of the secondary medical device from the luer connector treatment device 100 by detaching the secondary medical device from the female luer connector 111 will end fluid flow between the catheter and any secondary medical device. Additionally, the luer connectors of the luer connector treatment device 100 may be configured to prevent backflow of fluid when an external luer connector (belonging to the catheter or secondary medical device) is disengaged from its complementary luer connector in the luer connector treatment device as is depicted in FIG. 6.

In one embodiment, one or more of the luer connectors and/or components of the treatment chamber may be composed of transparent material such that UV radiation is able to be applied through the luer connectors into the interior of the treatment chamber 123. For example, each of the luer connectors may be composed of any combination of transparent polycarbonate material, transparent acrylic, 4-methylpentene-1 based polyolefin (TPX), fused silica, calcium fluoride, and the like. Each of the sources of UV radiation present in the first housing component or cap 101 and the second housing component or body 103 may be an ultraviolet light source such as a UV light emitting diode (LED), mercury vapor lamp, a xenon flash lamp, a continuous arc lamp, a UV laser, or any other UV light emitting device.

Each of the sources of UV radiation may emit a narrow spectrum light or broad spectrum light such as UV-A (315-400 nm wavelength), UV-B (280-315 nm wavelength), UV-C (100-280 nm wavelength), and the like. The ultraviolet light emitted by the UV source may be germicidal, or a substance or agent that destroys harmful microorganisms such as the microflora colonization believed to account for a majority of CRBSIs. As will be discussed further in the Example, one exemplary embodiment of the Luer connector treatment device may use UV-C light to effectively destroy 99.9% of bacteria.

Radiation (i.e., UV light) emitted from the sources of UV radiation may be emitted in a continuous or discrete manner. For example, UV light emitted from the sources of UV radiation may be generated in flashes and/or pulses that emit disinfecting light targeted towards the interior surfaces of the treatment chamber 123. The energy of a single flash or pulse may be sufficient to deliver a sterilizing or disinfecting dosage, e.g., approximately 40 mJ/cm$^2$ of UVC, to the surfaces of the treatment chamber 123. In one embodiment, each of the UV radiation sources contained within the second housing component or body 103 emits light in an area encompassing an approximately one hundred and twenty (120) degree arc from the UV radiation source. In one embodiment, each of the UV radiation sources in the second housing component or body 103 emits light in a direction generally radial to the axis A. In one embodiment, each of the UV radiation sources 107 in the first housing component or cap 101 emits light in a direction along the axis A into the treatment chamber 123.

The first housing component or cap 101 may have a first end 129 spaced apart from a second end 127 that is configured to reversibly couple with the second end 125 of the second housing component or body 103. In the embodiment depicted in FIG. 1, the first housing component or cap 101 has a protruding element 105 that is configured to engage with a receiving element 131 located on the second housing component or body 103. For example, the receiving element 131 may include a groove configured to receive the protruding element 105. Alternate attachment means may be used. In one embodiment, the first housing component or cap 101 may align with the second housing component or body 103 along a central axis A.

It is envisioned that a locking mechanism may be used in connection with the first housing component or cap 101 and second housing component or body 103 so as to keep the first housing component or cap 101 and second housing component or body 103 engaged with each other.

In one embodiment, parts of the first housing component or cap 101 and second housing component or body 103 may be composed of one or more materials including acrylic, polycarbonate, polyethylenimine (PEI), polyetheretherketone (PEEK), polyvinylidene difluoride (PVDF), and the like. The luer connectors and/or housing components may be composed of one or more of transparent polycarbonate material, transparent acrylic, 4-methylpentene-1 based polyolefin, fused silica, calcium fluoride, and the like. The materials for the construction of the first housing component or cap 101 and second housing component or body 103 may be chosen so that transmittance of UV radiation to the external environment is minimized. Furthermore, the materials for the construction of the first housing component or cap 101 and second housing component or body 103 may be chosen for stability after exposure to UV-C and chemicals or drugs typically introduced in catheter systems and for resistance to degradation. The materials for the first housing component or cap 101 and second housing component or body 103 may also be chosen so that the first housing component or cap 101 and second housing component or body 103 are capable of being manufactured by injection molding, thermoforming, compression molding, 3D printing, and the like.

In one embodiment, the luer connector treatment device 100 described herein may be constructed from low-cost material such that the device is disposable. Alternatively, the luer connector treatment device 100 may be constructed from materials that allow it to be reused and repeatedly sterilized by means such as autoclaving, gamma irradiation and the like. The materials chosen for the construction of the luer connector treatment device 100 may be designed such that the device does not need to be replaced or removed for the duration of the catheter in the patient's body.

In one embodiment, the at least one source of UV radiation embedded within the first housing component or cap 101 may be configured to emit UV radiation into the treatment chamber 123 only when the first housing component or cap 101 is engaged with the second housing component or body 103. Alternatively, the at least one source of UV radiation embedded within the first housing component or cap 101 may be configured to emit UV radiation into the treatment chamber 123 when the first housing component or cap 101 is disengaged with the second housing component or body 103. In one embodiment, the at least one source of UV radiation of the second housing component or body 103 may be configured to emit UV radiation into the treatment chamber when the first housing component or cap 101 is engaged with the second housing component or body 103 or when the first housing component or cap 101 is disengaged with the second housing component or body 103. In this manner, UV radiation may be used to treat the luer connector while the catheter is used (i.e., fluid is being pushed into or out of the catheter), and/or the catheter is engaged with a secondary medical device. Alternatively, in some embodiments, the UV radiation may not be applied while the catheter is being used (i.e., fluid is pushed into or out of the catheter).

Figure 2:
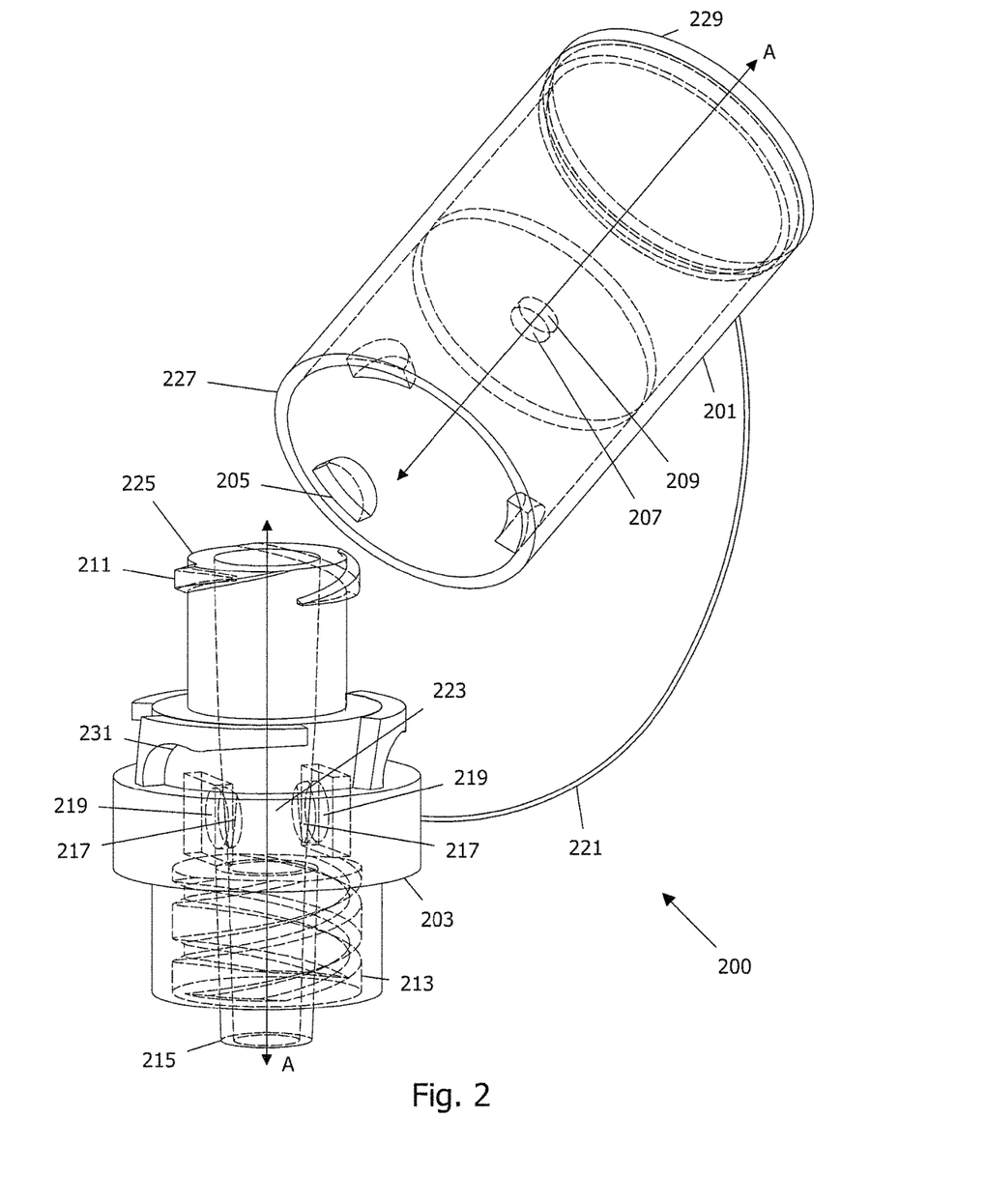
FIG. 2 illustrates a perspective view of a second exemplary embodiment of the device.

FIG. 2 illustrates a second embodiment of a luer connector treatment device 200 having similar components to those described above with respect to the luer connector treatment device 100 depicted in FIG. 1. The luer connector treatment device 200 includes a first housing component or cap 201 having a first end 229 spaced apart from a second end 227 that is configured to engage with a second housing component or body 203. The first housing component or cap 201 may have one or more apertures 209 configured to hold one or more sources of UV radiation 207.

The first housing component or cap 201 may also include one or more protrusions 205 that are configured to engage with the one or more slots 231 on the second housing component or body 203 of the catheter treatment device 200. In one embodiment, the first housing component or cap 201 may engage with the second housing component or body 203 in a twist and lock mechanism. In particular, as depicted, the slots 231 may contain hooks that are the inverse shape of the protrusions 205 on the cap 201. The first housing component or cap 201 may engage with the second housing component or body 203 by bringing the first housing component or cap 201 into contact with the second housing component or body 203 in a manner that aligns the two components on axis A, and twisting one of the housing components with respect to the other until the protrusions 205 engage with the hooks in the slots 231. Alternate mechanisms for engaging the first housing component or cap 201 to the second housing component or body 203 may be used. In one embodiment, the first housing component or cap 201 may be tethered or secured to the second housing component or body 203 by a cable 221 or other means. The cable 221 may be flexible and hollow. Alternate means to couple the first housing component or cap 201 to the second housing component or body 203 may be used.

The second housing component or body 203 of the luer connector treatment device 200 may include a treatment chamber 223 having a female luer connector 211 spaced apart from a male luer connector 213. The male luer connector 213 may be located proximate the first end 215 of the second housing component or body 203 that is configured to engage with a catheter. The female luer connector 211 may be located proximate the second end 225 of the body 203 that is configured to engage with a secondary medical device. A fluidic channel (as described above) may be formed between the two luer connectors. The second housing component or body 203 of the luer connector treatment device 200 may include one or more apertures 217, each configured to hold sources of UV radiation 219.

Figure 3:
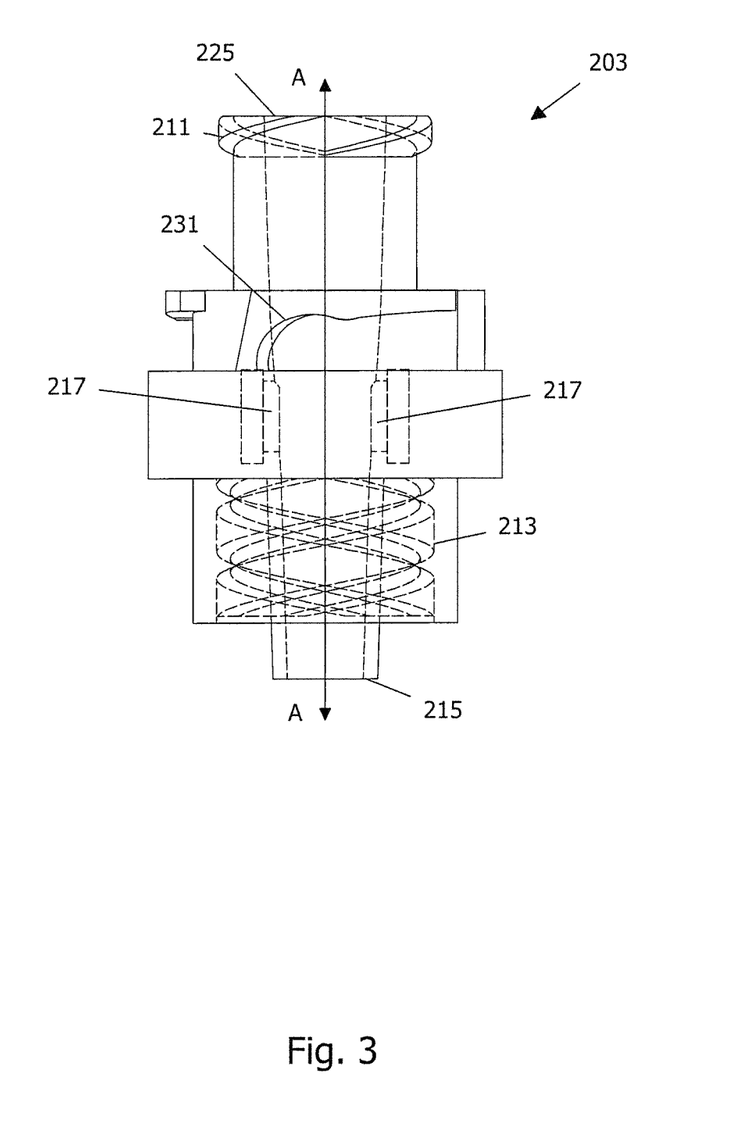
FIG. 3 illustrates a cross-sectional view of the second housing component depicted in FIG. 2.
Figure 4:
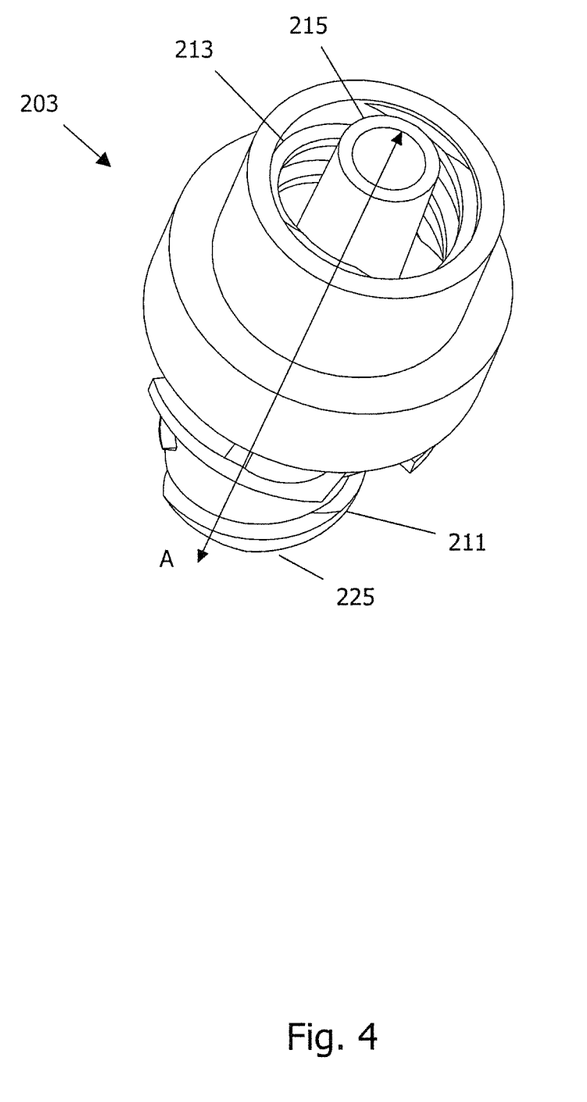
FIG. 4 illustrates a bottom perspective view of the secondary housing component depicted in FIGS. 2-3.
Figure 5:
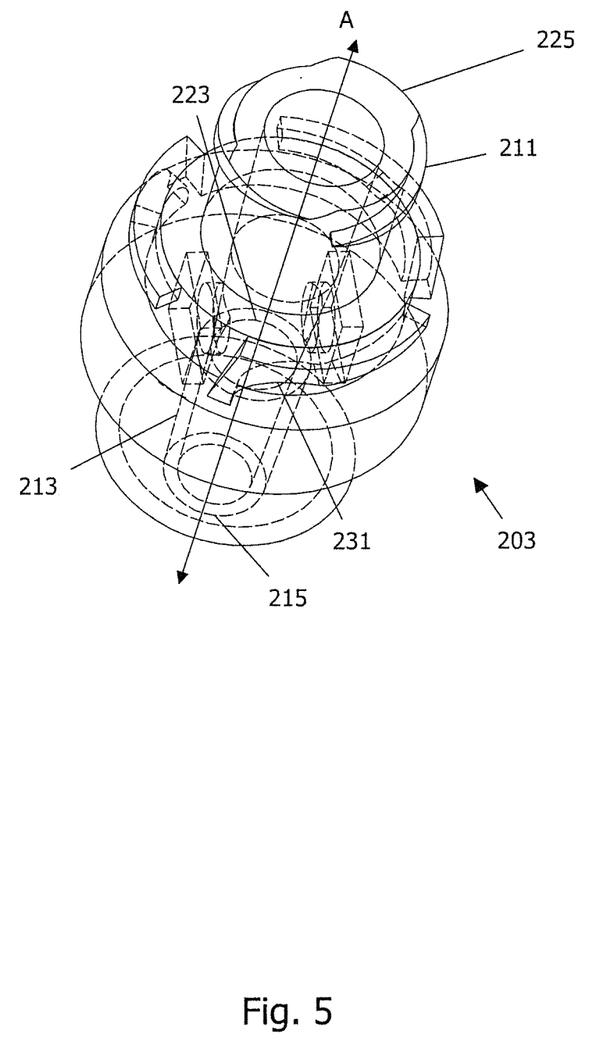
FIG. 5 illustrates a top perspective view of the secondary housing component depicted in FIGS. 2-4.

FIG. 3 illustrates a cross-sectional view of the second housing component or body 203 depicted in FIG. 2. FIG. 4 illustrates a bottom perspective view of the second housing component or body 203 depicted in FIGS. 2-3. FIG. 5 illustrates a top perspective view of the second housing component or body 203 depicted in FIGS. 2-4.

FIG. 6A illustrates a first perspective view of a second housing component or body 203 of another exemplary embodiment of the luer connector treatment device. FIG. 6B illustrates a cross-sectional view of the second housing component or body 203 depicted in FIG. 6A. FIG. 6C illustrates a second perspective view of the second housing component or body 203 depicted in FIGS. 6A-6B.

The depicted embodiment includes additional components 224 configured to prevent the backflow of fluids. For example, the treatment chamber may include a first portion having an inner diameter smaller than that of a second portion. The first portion may be hollow. An additional component 224 having a diameter approximately equivalent to that of the first portion may be situated in the first portion of the treatment chamber such that the treatment chamber is occluded and fluid flow is prevented from the first portion to the second portion of the treatment chamber and from the second portion to the first portion of the treatment chamber. When a secondary medical device such as a syringe engages with the at least one luer connector 211 of the second housing component or body 203, the external medical device may cause the additional component 224 to lower into the broader second portion of the treatment chamber and allow fluid to flow from the catheter to the syringe or the syringe to the catheter.

Figure 7:
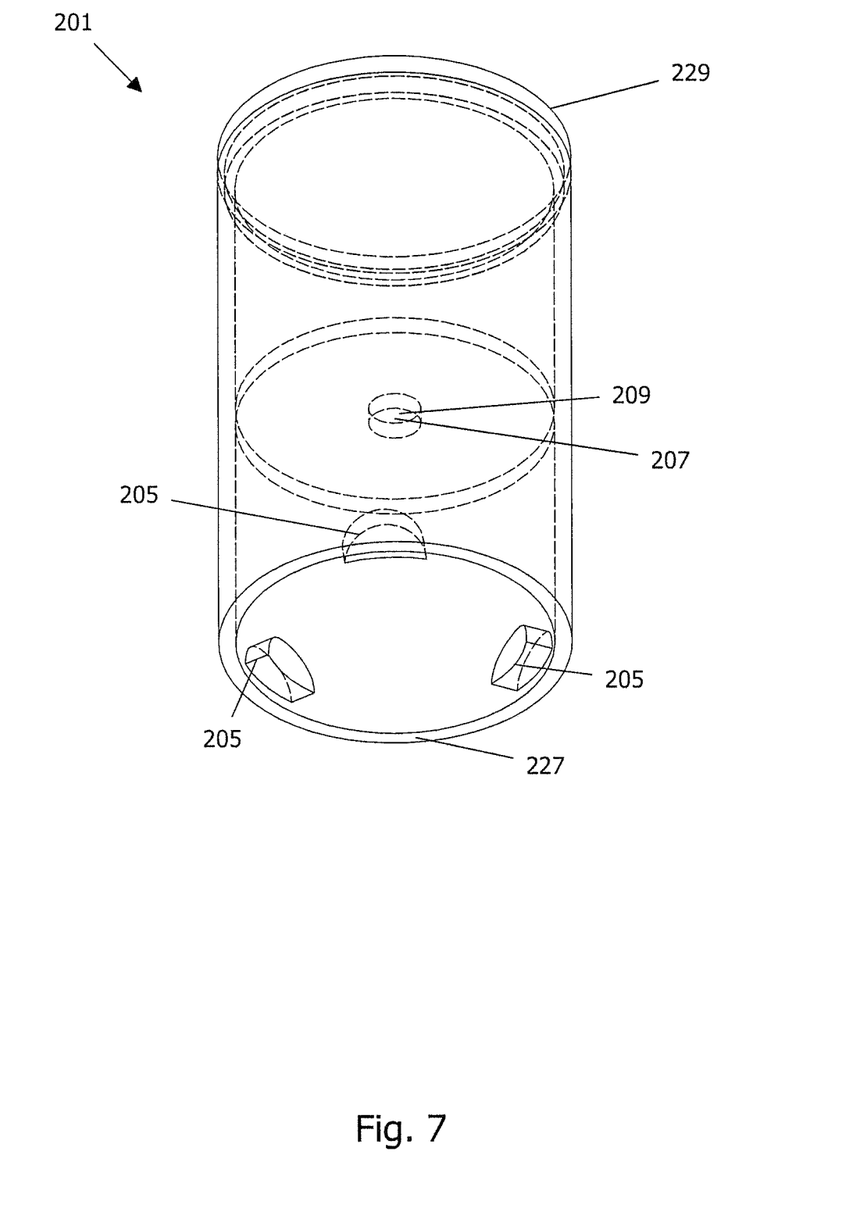
FIG. 7 illustrates a perspective view of the first housing component depicted in FIG. 2.

FIG. 7 illustrates a perspective view of the first housing component 201 depicted in FIG. 2.

Figure 8:
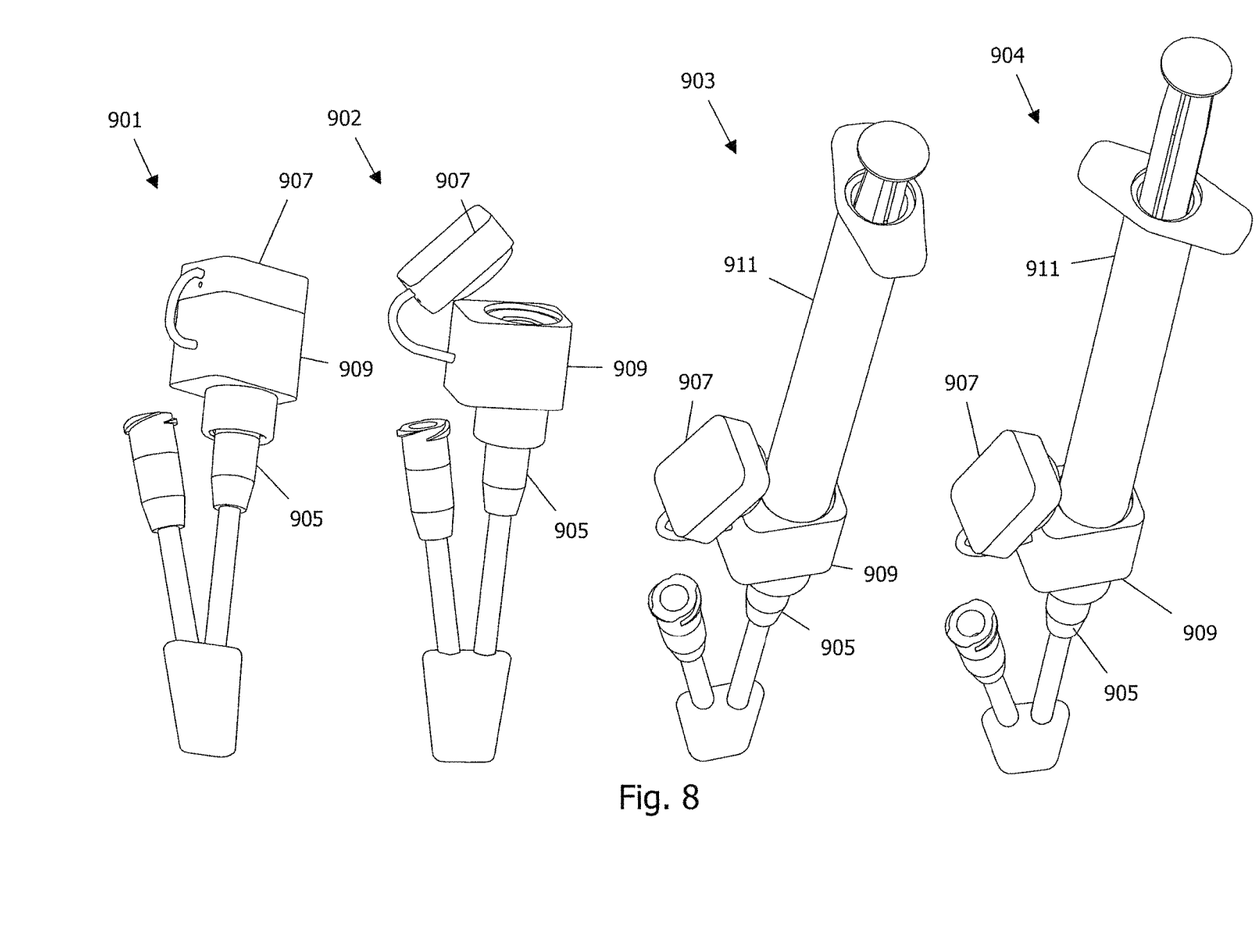
FIG. 8 illustrates the operation of an embodiment of the luer connector treatment device.

Steps of a process associated with a specific embodiment are depicted in FIG. 8. In a first step 901, a first medical device (catheter) 905 is attached to the luer connector treatment device having a first housing component or cap 907 and second housing component or body 909. In a second step 902, the first housing component or cap 907 is removed or disengaged from the second housing component or body 909. In a third step 903, a second medical device (syringe) 911 is attached to the luer connector treatment device. The second medical device 911 may be attached to the luer connector treatment device by being screwed on, pierced, or any alternate means of attaching to one or more luer connectors within the treatment chamber. The second medical device 911 may then be used in accordance with its normal function to withdraw blood and/or deliver medical treatments, as is depicted in a fourth step 904. During at least one of steps one 901 to four 904, UV radiation may be applied to the contents of the treatment chamber that is located within the second housing component or body 909 by way of one or more sources of UV radiation present in accordance with the structure, methods and systems described above.

Different combinations of UV sources may be configured to turn on for the duration of each step to ensure safety and optimize UV delivery to surfaces of the treatment chamber. For example, the at least one source of UV in the first housing component or cap 907 may be turned off while any UV sources in the second housing component or body 909 may be turned on when the first housing or cap 907 is disengaged from the second housing component or body 909. This ensures that sterility is maintained within the treatment chamber and users will be protected from UV light that may emit from the first housing component or cap 907.

The sources of UV radiation described above with respect to FIGS. 1-8 may be controlled by mechanical, electrical, or electromechanical means, or any other suitable means. In one embodiment, each of the sources of UV radiation may be powered by one or more batteries or power supplies distributed about the first housing component 101, 201 and/or second housing component 103, 203. For example, the luer treatment device may be configured to be powered from a wall outlet and the like. Alternatively, the batteries and/or power supplies may be a separate component attached to at least one of the first housing component 101, 201 and second housing component 103, 203. Suitable batteries for use with the described embodiments include coin cell batteries, N batteries, and the like. Wired connections between the sources of UV radiation and the batteries may extend from the first housing component 101, 201 to the second housing component 103, 203. The wired connectors may be enclosed within a cable, such as the flexible cable 221 depicted in FIG. 2.

The microcontroller may be configured to detect when a first housing component is engaged with or disengaged from a second housing component, and control the operation of the sources of UV radiation present in the first housing component and second housing component based on the detected information.

The microcontroller can be combined with mechanical switches to control the operation of the sources of UV radiation. In one embodiment, a microcontroller may be located on a first housing component or cap 101, 201 of a luer connector treatment device 100, 200. The microcontroller may be powered by one or more batteries located on a first housing component or cap 101, 201. Alternatively, the one or more batteries may be located on the second housing component or body 103, 203 of the luer connector treatment device 100, 200 or a combination of both the first housing component and second housing component or a separate third housing component. Alternatively, the microcontroller may be located on the second housing component or body 103, 203 of the luer connector treatment device 100, 200. In one embodiment, power may be provided to the microcontroller, switches, and other electrical components located in the first or second housing component of the luer connector treatment device 100, 200 from the one or more batteries by way of one or more electrical connections stored in a flexible cable 221.

The microcontroller may receive input from one or more switches. For example, in one embodiment, the microcontroller receives input from an override switch and a cap/sensor switch. The override switch may toggle between two settings: a default/off setting and an override/on setting. In the default/off setting, the one or more of the sources of UV radiation may be controlled so as not to emit UV radiation. In the override/on setting, the one or more sources of UV radiation may be controlled so as to emit UV radiation. The override switch may be configured to control the operation of the sources of UV radiation in only the second housing component or body 103, 203, or both the second housing component and the first housing component or cap 101, 201. The override switch may be configured to receive input from medical personnel or other users.

The cap/sensor switch may include one or more mechanical elements that are configured to send one or more signals to the microcontroller indicating whether the first housing component or cap 101, 201 is engaged with the second housing component or body 103, 203. Alternatively, non-mechanical elements may be used as a part of the cap/sensor switch to indicate whether the first housing component or cap 101, 201 is engaged with the second housing component or body 103, 203. In one embodiment, a mechanical element extends along the surface of the second housing component that is configured to engage with the first housing component. For example, when the first housing component 201 is configured to engage with the second housing component 203 in a twist-and-lock mechanism, as is described above, a switch may be positioned on a hook such that the groove on the first housing component pushes the switch inwards along the second housing component. In response to the switch being pushed inwards, a signal may be sent to the microcontroller. In one embodiment, the signal may cause a change in the voltage that is transmitted to the microcontroller. For example, a first signal and associated voltage may be associated with the first housing component or cap 101, 201 being engaged with the second housing component or body 103, 203 and a second signal and associated voltage may be associated with the first housing component or cap being disengaged with the second housing component or body. In one embodiment, the cap/sensor switch may include a photodiode, proximity sensor and the like.

In one embodiment, the microcontroller, override, and a cap/sensor switch may work in unison to provide UV radiation to the treatment chamber. A summary describing how the microcontroller, override, and cap/sensor is in Table 1. In the illustrated embodiment, the override switch sensor has two possible statuses: on or off. The cap/sensor switch may have two statuses: off, which indicates that the first housing component or cap 101, 201 is detached from the second housing component or body 103, 203, and on, which indicates that the first housing component or cap 101, 201 is attached to the second housing component or body 103, 203.

In the embodiment described in Table 1, UV radiation may be emitted by the sources of UV radiation located on the first housing component or cap 101, 201 when the override switch is either in an on or off state, and the cap/sensor switch is in the on state. Notably, while the override switch is either in an on or off state, and the cap/sensor switch is in the on state, UV radiation may not be emitted from the sources of UV radiation located on the second housing component or body 103, 203. When the override switch is in an off state, and the cap/sensor switch is in an off state, in one embodiment, the Luer connector treatment device may be configured so that UV radiation may is not emitted from the first housing component, or cap, 101, 201 and/or the second housing component or body 103, 203. In the embodiment described in Table 1, when the override switch is in an on state and the cap/sensor switch is in an off state, UV radiation may not be emitted by sources of UV radiation located on the first housing component or cap, while UV radiation is emitted by sources of UV radiation located on the second housing component or body.

TABLE 1

| Override Switch State | Cap/Sensor Switch State | State of sources of UV radiation located on the first housing component or cap | State of sources of UV radiation located on the second housing component or body |
|---|---|---|---|
| Off/On | On | On | Off |
| Off | Off | Off | Off |
| On | Off | Off | On |

Advantageously, when the microcontroller and related components are configured as is described in Table 1, UV radiation is applied to the treatment chamber by either the first housing component or cap 101, 201, or by the second housing component or body 103, 203. In the configuration above, UV radiation is applied by the first housing component or cap 101, 201, when the first housing component or cap 101, 201 is attached to the second housing component or body 103, 203. However, when the first housing component or cap 101, 201 is disengaged from the second housing component or body 103, 203, the treatment chamber is treated by UV radiation from the sources of UV radiation located within the second housing component or body 103, 203. In this manner, UV radiation may be applied even when a first housing component or cap 101, 201 is removed from the second housing component or body 103, 203, as is necessary when engaging a second medical device with the luer connector treatment device. Furthermore, in the configuration of the microcontroller described in Table 1, all of the sources of UV radiation may be turned off (non-emitting) until the override switch is moved to an on state. This may be advantageous in the administration of pharmaceuticals or other medical techniques that are sensitive to UV radiation. For example, chemotherapy medications are known to interact with UV radiation. Accordingly, having a microcontroller system in which a medical personnel is required to change the status of the override switch to the on state prior to emitting UV radiation, prevents the inadvertent administration of UV radiation when the first housing component or cap 101, 201 is disengaged from the second housing component of body 103, 203.

In an exemplary embodiment, additional sensors may be used to detect when an external medical device is attached to the second housing component or body 103, 203. Input from these additional sensors may be used to determine whether UV radiation should be applied to the treatment chamber. Suitable sensors include (but are not limited to) photodiodes, proximity sensors, mechanical switches. The sensors may undergo a voltage change when an external medical device is attached to the luer connector treatment device. The voltage change may then be connected to an input pin of the microcontroller, causing the microcontroller to turn on one or more UV LEDs. For example, a voltage change detecting the insertion of an external medical device into the second housing component or body 103, 203 may trigger the microcontroller to turn on one or more UV LEDs in the second housing component or body. This function advantageously helps automatically sterilize external medical devices and their contents to prevent any microflora from the environment from being transferred into the treatment chamber and subsequently the luer connector (i.e. catheter hub) the luer connector treatment device is connected to.

Although electromechanical means for detecting the engagement or disengagement of the first housing component or cap 101, 201 to the second housing component or body 103, 203 are described above, it is contemplated that alternate means may be used.

The luer connector treatment device may also include an alert component that is configured to notify a user of the state of the luer connector treatment device and/or the sources of UV radiation. For example, in one embodiment, electrical outputs from the microcontroller may output to a boost converter (optional) routed through LED drivers (optional) and finally output to one or more UV LEDs. In one embodiment, these components may be arranged in series. The boost converter may increase the voltage of the electrical outputs to a sufficient level that causes the UV LEDs to turn on. The LED drivers may be used to stabilize the current that is input into the UV LEDs. At least one visible wavelength LED with wavelengths within the range of approximately 390 to 700 nm may be placed in series, parallel, or both to the at least one UV LED. The visible wavelength LEDs may be configured to turn on when the microcontroller output indicates that UV radiation is being emitted by the one or more of the sources of UV radiation in the luer connector treatment device. For example, in one embodiment, microcontrollers that output a high voltage may cause the one or more downstream UV LEDs to turn on, and subsequently the visible wavelength LEDs to turn on. Similarly, when microcontrollers output a low voltage, downstream visible wavelength LEDs may be turned off.

In an alternate embodiment, photochromic pigments may be used as a part of the alert component. For example, photochromic pigments that change color based on UV radiation intensity may be used to indicate the wavelength of UV radiation emitted by the sources of UV radiation. In some embodiments, the photochromic pigments may be reversible. Systems may also be in place to alert users of the battery life using electrical components or chemical means, such as material containing thermochromic pigments that change color as the battery life decreases leading to changes in temperature.

Alternatively, a circuit containing photodiodes, transistors and/or amplifiers may be used as a part of the alert component. For example, photodiodes may detect the presence of UV radiation by generating an electrical current that is used to light an LED and alert a user of the emission of UV radiation. Additionally, the microcontroller may be configured to periodically monitor the levels of one or more batteries. Once the battery voltage falls below a certain threshold, the microcontroller may be configured to cause a visible wavelength LED to light up to alert users.

In another alternate embodiment, a failure detection circuit may be used to alert a user of the presence of UV radiation. For example, comparators may be configured to compare the voltage from a UV radiation emitting source to a control voltage emitter. The comparators may output different voltages indicating the result of the comparison, the output voltages being used to illuminate one or more visible wavelength LEDs. It is contemplated that alternate alert components may also be used.

Embodiments of the luer connector treatment device described herein may be used as an add-on to existing catheters. Alternatively, the described luer connector treatment device may be integrated into a catheter or other medical device. For example, the luer connector treatment device may replace the catheter hub and be permanently attached to a catheter, in which the inner lumen of the male luer connector 213 is partially connected to the catheter lumen and at least one remaining female luer connector 211 may be attached to a secondary medical device.

EXAMPLES

Figure 9:
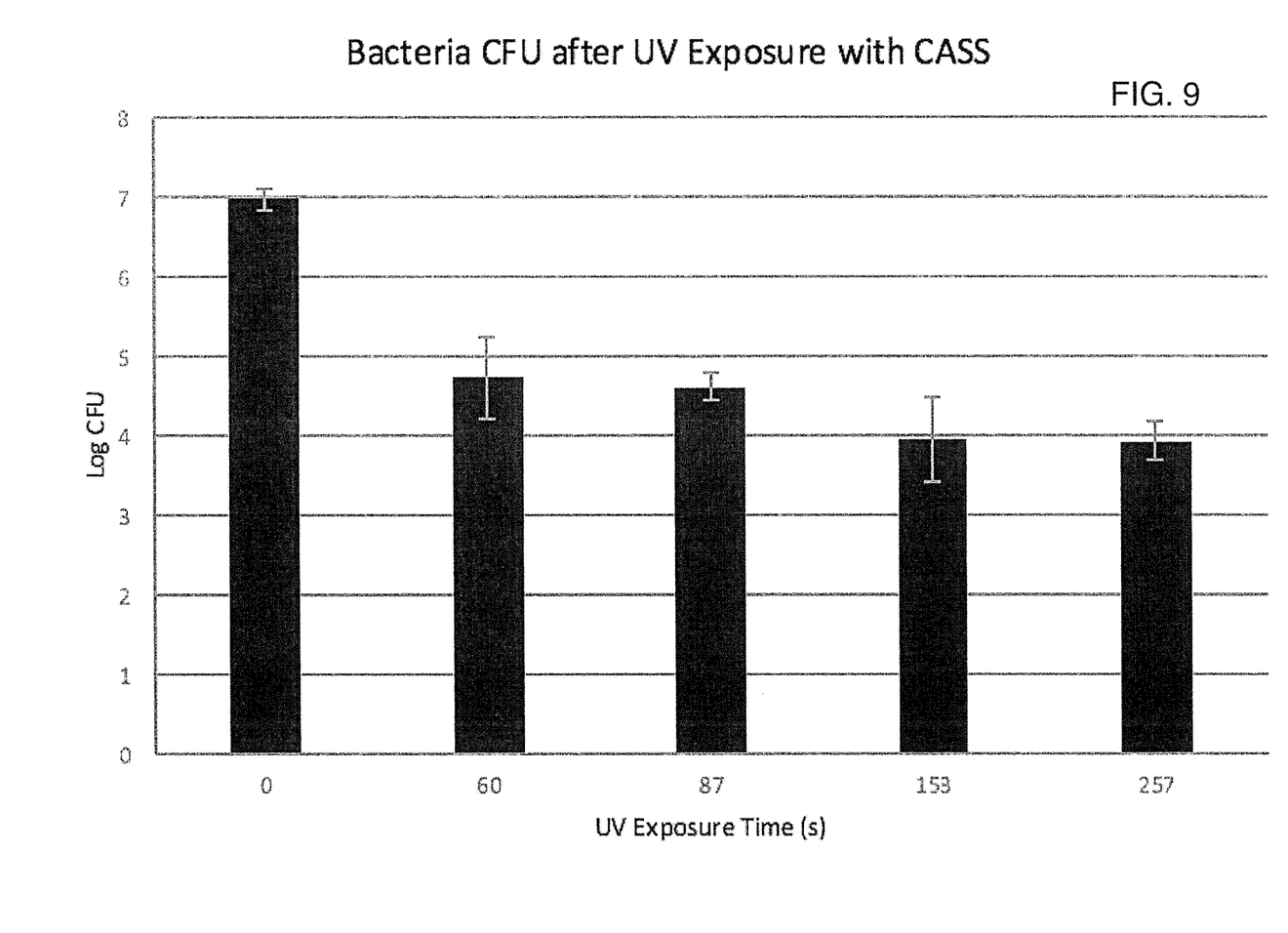
FIG. 9 illustrates results from an experimental setup used in connection with the luer connector treatment device.

As illustrated in FIG. 9, experiments were conducted to study the efficacy of using UV radiation emitting LEDs to eradicate bacteria on luer connectors used in catheter hubs and the like.

In particular, the first and second housing components of the luer connector treatment devices were sterilized with 70% ethanol and left to air dry at room temperature in a disengaged state. A bacterial suspension solution of 0.3 OD Staphylococcus aureus was diluted 100× with tryptic soy broth. To inoculate the second housing components of the devices, the second housing components were entirely immersed in the bacterial suspension for three hours. The second housing components were then removed from the bacterial suspension and left to air dry for 30 minutes.

The first housing components were then engaged with their respective second housing components. UV light sources located within the first housing components were turned on for a specified duration of time. The specified durations of times included 0 (control), 60, 87, 153 and 257 seconds.

Data was collected for each sample by dipping a sterile swab in tryptic soy broth and then swabbing the inner lumen of the second housing component (i.e., treatment chamber). The amount of sample collected from each swab was controlled by performing a 360 degree motion three times towards the lower half of the lumen and three times towards the upper half of the lumen. Each swab was placed in a separate sterile test tube filled with 2 mL of tryptic soy broth. The swabs immersed in the broth were gently shaken for thirty seconds to transfer the bacteria from the swabs into the broth.

The swabs were then removed and the test tubes vortexed at 50% of the highest setting for one minute. 200 uL was pipetted from the suspension in each test tube and transferred to an agar plate. The pipetted suspensions were spread evenly across the agar plates using a glass spreader. The plates were incubated overnight at 37 degrees Celsius for at least 20 hours. The number of colonies that formed on each plate were then counted.

The average colony forming units (CFUs) found for each plate is shown in FIG. 9. As illustrated, there is a general downwards trend in average CFUs as UV exposure duration increases. After performing a two-tailed, homoscedastic T-test with a significance level of 0.01, it was found that all groups had significantly different CFUs compared to that of the control (no UV exposure). The CFU log reductions from the control group were 2.24, 2.35, 3.03, and 3.04 for groups exposed to 60, 87, 153 and 257 seconds of UV, respectively.

The results from the experiment suggest that given the geometry of the device, bacterial eradication can be achieved. At least a range of 2.24 to 3.04 log reduction, or in other words a 99.4% to 99.9% can be achieved using the luer connector treatment device. The amount of bacterial reduction varies depending on the length of UV exposure.

Particularly, the results simulate a scenario in which all of the inner surfaces of the sterilization device are contaminated at once with 0.3 OD of Staphylococcus aureus. In clinical settings, it is expected that the bacterial load on the device may be lower, which can potentially lead to greater bacterial reductions. In addition, the devices tested were 3D printed with 3D-printing resin. Different materials and manufacturing methods may affect the results.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A luer connector treatment device comprising:
a first housing component having at least one source of UV radiation; and
a second housing component reversibly coupled to said first housing component, the second housing component further comprising
a treatment chamber disposed therein and including at least two luer connectors formed in at least one surface of the second housing component, and
at least one source of UV radiation;
wherein the at least one source of UV radiation of the first housing component is configured to emit UV radiation into the treatment chamber when the first housing component is engaged with or disengaged from the second housing component, and
wherein the at least one source of UV radiation of the second housing component is configured to emit UV radiation into the treatment chamber when the first housing component is engaged with or disengaged from with the second housing component.

2. The luer connector treatment device of claim 1, wherein at least one source of UV radiation of the first housing component and the second housing component is UV-C radiation having a wavelength between about 100 nanometers to about 280 nanometers.

3. The luer connector treatment device of claim 1, wherein the at least one source of UV radiation of the first housing component is configured to emit UV radiation into the treatment chamber along a generally axial length of the treatment chamber.

4. The luer connector treatment device of claim 1, wherein the at least one source of UV radiation of the second housing component is configured to emit UV radiation into the treatment chamber along an angled direction within the treatment chamber.

5. The luer connector treatment device of claim 1, wherein the first housing component is reversibly coupled to the second housing component by attachment means.

6. The luer connector treatment device of claim 1, wherein at least one of the at least one source of UV radiation of the first housing component and the at least one source of UV radiation of the second housing component is a light emitting diode (LED).

7. The luer connector treatment device of claim 1, wherein a fluid channel is formed within the treatment chamber when a first medical device is engaged with one luer connector of the at least two luer connectors and a second medical device is engaged with a second luer connector of the at least two luer connectors.

8. The luer connector treatment device of claim 1, wherein at least one of the at least one source of UV radiation of the first housing component and the at least one source of UV radiation of the second housing component is powered by one or more batteries, each of the one or more batteries disposed within at least one of the first housing component, the second housing component, and an additional housing component.

9. The luer connector treatment device of claim 1, wherein at least one of the first housing component and the second housing component further comprises at least one integrated circuit configured to:
   detect when the first housing component is one of engaged with and disengaged from the second housing component.

10. The luer connector treatment device of claim 1, wherein at least one of the first housing component and the second housing component further comprises at least one integrated circuit configured to:
   control operation of at least one of the at least one source of UV radiation of the first housing component and at least one of the at least one source of UV radiation of the second housing component.

11. The luer connector treatment device of claim 1, further comprising an override switch configured to at least one of enable and disable one or more of the at least one source of UV radiation of the first housing component and at least one source of UV radiation of the second housing component.

12. The luer connector treatment device of claim 1, wherein at least a portion of at least one of the first housing component and the second housing component is composed of at least one of acrylic material, polycarbonate, polyethylenimine (PEI), polyetheretherketone (PEEK), and polyvinylidene difluoride (PVDF).

13. The luer connector treatment device of claim 1, wherein at least one of the at least one luer connector and second housing component is at least partially transparent to UV radiation.

14. The luer connector treatment device of claim 1, wherein the first housing component and second housing component are manufactured via at least one of injection molding, thermoforming, compression molding, 3D printing.

15. The luer connector treatment device of claim 1, further comprising an alert component configured to notify a user of the luer connector treatment device of a status of at least one of the at least one source of UV radiation of the first housing component and the at least one source of UV radiation of the second housing component.

16. The luer connector treatment device of claim 1, further comprising an alert component configured to notify a user of the luer connector treatment device of the status of at least one battery configured to provide power to the at least one source of UV radiation.

17. The luer connector treatment device of claim 1, wherein the treatment chamber further comprises at least one fluidic channel formed by the at least two luer connectors formed in the at least one surface of the second housing component.

18. A luer connector treatment device comprising:
   a housing component further comprising a treatment chamber disposed therein, said treatment chamber including at least two luer connectors formed in at least one surface of the housing component;
   an occlusion component mechanism coupled to the housing component that reversibly occludes the treatment chamber from an external environment;
      wherein the housing component has at least one source of UV radiation configured to emit UV radiation into the treatment chamber.

19. The luer connector treatment device of claim 18, wherein the occlusion component is reversibly coupled to and separate from the housing component.

20. The luer connector treatment device of claim 18, wherein the occlusion component is contained within or on the housing component.

21. The luer connector treatment device of claim 18, wherein the at least one source of UV radiation of the housing component is configured to emit UV radiation into the treatment chamber when the occlusion component occludes or un-occludes the treatment chamber.

22. The luer connector treatment device of claim 18, wherein the occlusion component is contained within a second housing component.

23. The luer connector treatment device of claim 22, wherein the second housing component further comprises at least one source of UV radiation configured to emit UV radiation into the treatment chamber.

24. The luer connector treatment device of claim 18, wherein the treatment chamber further comprises at least one fluidic channel formed by the at least two luer connectors formed in the at least one surface of the housing component.

* * * * *